US009649490B2

(12) United States Patent
Booker

(10) Patent No.: US 9,649,490 B2
(45) Date of Patent: May 16, 2017

(54) TIP FOR LEAD EXTRACTION DEVICE

(75) Inventor: Robert Booker, Vandergrift, PA (US)

(73) Assignee: Cook Medical Technologies LLC, Bloomington, IN (US)

(*) Notice: Subject to any disclaimer, the term of this patent is extended or adjusted under 35 U.S.C. 154(b) by 207 days.

(21) Appl. No.: 13/161,986

(22) Filed: Jun. 16, 2011

(65) Prior Publication Data

US 2012/0323252 A1    Dec. 20, 2012

(51) Int. Cl.
    *A61B 19/00*     (2006.01)
    *A61N 1/05*     (2006.01)
    *A61B 17/34*     (2006.01)
    *A61B 17/32*     (2006.01)
    *A61B 17/3205*     (2006.01)
    *A61B 17/29*     (2006.01)

(52) U.S. Cl.
    CPC ...... *A61N 1/056* (2013.01); *A61B 17/320016* (2013.01); *A61B 17/32053* (2013.01); *A61B 17/3468* (2013.01); *A61B 2017/2903* (2013.01); *A61B 2017/2924* (2013.01); *A61N 2001/0578* (2013.01); *A61N 2001/0585* (2013.01)

(58) Field of Classification Search
    CPC ........ A61B 17/3468; A61B 17/320016; A61B 17/3207; A61B 17/3205; A61B 17/32; A61B 17/320758; A61B 17/32002; A61B 2017/320072; A61B 2017/320076; A61B 2017/320044; A61B 2017/320056; A61B 17/32096; A61N 2001/0578; A61F 2/95; A61F 2002/9528
    USPC ........ 606/129, 222–223, 311, 191, 301, 305, 606/308, 318, 321, 96
See application file for complete search history.

(56) References Cited

U.S. PATENT DOCUMENTS

| | | | |
|---|---|---|---|
| 2,261,230 A | 11/1941 | Cox et al. ............... | 128/310 |
| 3,132,549 A | 5/1964 | Lee ..................... | 81/57 |
| 3,519,046 A | 7/1970 | Pierce ................. | 145/66 |
| 3,756,090 A | 9/1973 | Mella et al. | |
| 4,030,503 A | 6/1977 | Clark, III .............. | 128/304 |
| 4,084,594 A | 4/1978 | Mosior ................. | 128/311 |
| 4,174,858 A | 11/1979 | Brooks ................. | 285/7 |
| 4,576,162 A * | 3/1986 | McCorkle ............. | A61B 17/29 |
| | | | 294/100 |
| 4,643,190 A | 2/1987 | Heimberger .......... | 128/321 |

(Continued)

FOREIGN PATENT DOCUMENTS

| | | | | |
|---|---|---|---|---|
| EP | 0 807 412 A1 | 11/1997 | ............ | A61B 17/22 |
| EP | 1 820 458 A1 | 8/2007 | ............ | A61B 17/22 |

OTHER PUBLICATIONS

Albee, F. "Bone Surgery with Machine Tools," Scientific American, Apr. 1936, pp. 178-181.

*Primary Examiner* — Melanie Tyson
(74) *Attorney, Agent, or Firm* — Brinks Gilson & Lione

(57) ABSTRACT

A tip engageable with an elongated sheath member for extracting a cardiac lead from an obstruction in a body vessel of a patient. The tip includes a tip body having a proximal end, a distal end, and a passageway extending therethrough. The tip body proximal end is engageable with the distal end of the sheath member distal end. The passageway of the tip is aligned with the passageway of the sheath such that the cardiac lead is receivable therein. The tip body distal portion has a plurality of sides extending circumferentially therearound, wherein the sides have respective ends and an inwardly directed radiused portion between the ends.

19 Claims, 6 Drawing Sheets

(56) References Cited

U.S. PATENT DOCUMENTS

| | | |
|---|---|---|
| 4,943,289 A | 7/1990 | Goode et al. .................... 606/1 |
| 4,988,347 A | 1/1991 | Goode et al. .................... 606/1 |
| 5,011,482 A | 4/1991 | Goode et al. .................... 606/1 |
| 5,013,310 A | 5/1991 | Goode et al. .................... 606/1 |
| 5,052,402 A | 10/1991 | Bencini et al. .............. 128/751 |
| 5,092,848 A | 3/1992 | deCiutiis ...................... 604/170 |
| 5,122,134 A | 6/1992 | Borzone et al. ................ 606/80 |
| 5,207,683 A | 5/1993 | Goode et al. ................ 606/108 |
| 5,363,726 A | 11/1994 | Smith ......................... 81/57.29 |
| 5,423,806 A | 6/1995 | Dale et al. ..................... 606/15 |
| 5,447,534 A | 9/1995 | Jammet ........................ 607/127 |
| 5,507,751 A | 4/1996 | Goode et al. ................ 606/108 |
| 5,591,187 A | 1/1997 | Dekel |
| 5,632,749 A | 5/1997 | Goode et al. ................ 606/108 |
| 5,651,781 A | 7/1997 | Grace ................................ 606/1 |
| 5,697,936 A | 12/1997 | Shipko et al. ................ 606/108 |
| 5,769,858 A | 6/1998 | Pearson et al. .............. 606/108 |
| 5,814,044 A | 9/1998 | Hooven |
| 5,830,221 A | 11/1998 | Stein et al. ................... 606/151 |
| 5,830,231 A | 11/1998 | Geiges, Jr. ................... 606/205 |
| 5,913,857 A | 6/1999 | Ritchart et al. |
| 5,980,515 A | 11/1999 | Tu .................................. 606/41 |
| 5,980,545 A | 11/1999 | Pacala et al. ................. 606/170 |
| 5,984,939 A | 11/1999 | Yoon .............................. 606/170 |
| 5,993,467 A | 11/1999 | Yoon .............................. 606/147 |
| 6,010,476 A | 1/2000 | Saadat ............................ 604/22 |
| 6,099,537 A | 8/2000 | Sugai et al. |
| 6,135,947 A | 10/2000 | Watanabe et al. ........... 600/178 |
| 6,136,005 A | 10/2000 | Goode et al. ................ 606/108 |
| 6,190,353 B1 | 2/2001 | Makower et al. .............. 604/95 |
| 6,283,511 B1 | 9/2001 | Kamp ............................ 285/391 |
| 6,332,886 B1 | 12/2001 | Green et al. .................... 606/80 |
| 6,419,974 B1 | 7/2002 | Silva et al. .................... 426/580 |
| 6,451,036 B1 * | 9/2002 | Heitzmann ....... A61B 17/32075 606/159 |
| 6,503,261 B1 | 1/2003 | Bruneau et al. .............. 606/159 |
| 6,656,195 B2 * | 12/2003 | Peters ............. A61B 17/32002 606/159 |
| 6,687,548 B2 | 2/2004 | Goode .......................... 607/119 |
| 6,712,826 B2 | 3/2004 | Lui ................................ 606/108 |
| 6,712,855 B2 | 3/2004 | Martin et al. ............. 623/20.34 |
| 6,783,533 B2 | 8/2004 | Green et al. .................... 606/80 |
| 2002/0143358 A1 | 10/2002 | Domingo et al. ............ 606/190 |
| 2002/0172923 A1 | 11/2002 | Strong et al. ................. 433/165 |
| 2003/0040787 A1 | 2/2003 | Flynn et al. .................. 607/122 |
| 2003/0187447 A1 * | 10/2003 | Ferrante et al. ................ 606/73 |
| 2004/0143287 A1 | 7/2004 | Konstantino et al. ......... 606/194 |
| 2004/0260336 A1 | 12/2004 | Braun ........................... 606/205 |
| 2005/0107816 A1 | 5/2005 | Pingleton et al. ............ 606/185 |
| 2005/0273125 A1 | 12/2005 | Opie ............................. 606/159 |
| 2006/0235431 A1 | 10/2006 | Goode et al. ................ 606/108 |
| 2006/0253179 A1 | 11/2006 | Goode et al. ................ 607/115 |
| 2008/0058675 A1 * | 3/2008 | Shabaz ............. A61B 10/0275 600/567 |
| 2008/0071341 A1 | 3/2008 | Goode et al. ................ 607/122 |
| 2008/0071342 A1 * | 3/2008 | Goode ............. A61B 17/32002 607/122 |
| 2011/0172718 A1 * | 7/2011 | Felix et al. ................... 606/305 |
| 2011/0295319 A1 * | 12/2011 | Duplessis et al. ............ 606/264 |

\* cited by examiner

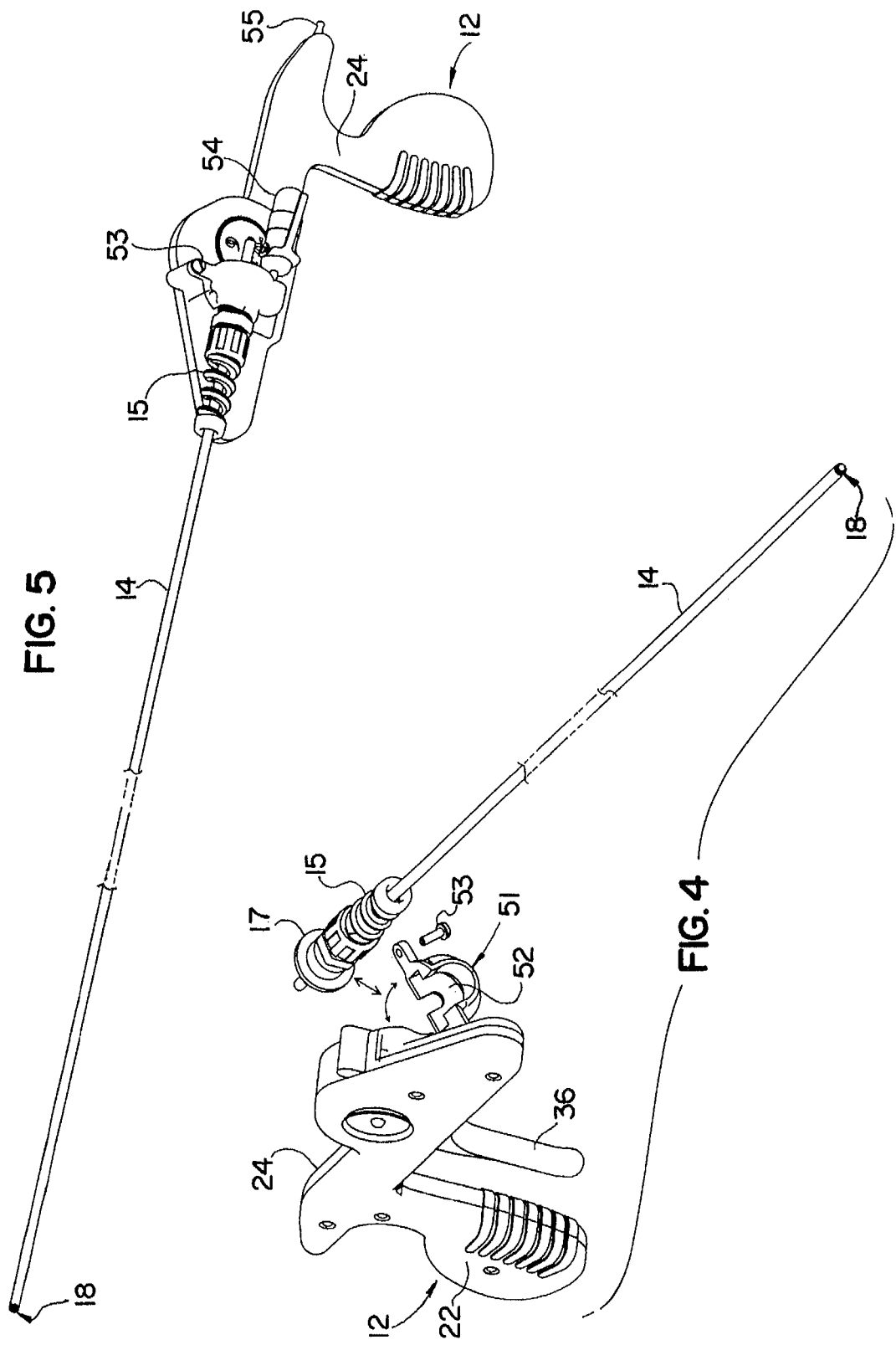

TIP FOR LEAD EXTRACTION DEVICE

BACKGROUND

1. Technical Field

This invention relates generally to a device for use in separating an implanted elongated structure from encapsulating tissue in the body of a patient. More particularly, the invention relates to a tip for an extraction device for use in separating a cardiac lead from encapsulating biological tissue.

2. Background Information

A variety of medical treatments and surgical methods entail implanting an elongated structure in the body of a patient. Examples of such elongated structures include catheters, sheaths and cardiac leads (such as pacemaker leads and defibrillator leads), as well as a variety of other devices. Over time, it can become necessary or desirable to remove the implanted elongated structure from the body of the patient. However, if the elongated structure has been implanted for an extended period of time, encapsulating biological tissue can grow around the elongated structure, making it difficult to remove the structure from the encapsulating tissue.

A heart pacemaker is typically implanted in a subcutaneous tissue pocket in the chest wall of a patient. A pacemaker lead extends from the pacemaker through a vein into a chamber of the patient's heart. The pacemaker lead commonly includes a conductor, such as an electrical wire coil, for conducting electrical signals (such as stimulating and/or sensing signals) between the pacemaker and the heart. Leads for defibrillators are generally similar to pacemaker leads, and are positioned about the heart. Defibrillator leads may be affixed either internally or externally of the heart.

While cardiac leads typically have a useful life of many years, over time such leads may become encapsulated by fibrotic tissue against the heart itself or the wall of the vein, against other surrounding tissue, or even against other cardiac leads in the vein. Encapsulation is especially encountered in areas where the velocity of the flow of blood is low. The fibrotic tissue can be very tough, which makes it difficult to remove the lead from the area of the heart without causing trauma to the area. When small diameter veins through which a cardiac lead passes become occluded with fibrotic tissue, separation of the lead from the vein can cause damage to the vein, including the possible dissection or perforation of the vein. In such cases, separation of the lead from the vein is usually not possible without restricting or containing movement of the lead, i.e., fixing the lead in position with respect to the patient, in particular, with respect to the patient's vein.

To avoid this and other possible complications, some useless or otherwise inoperable cardiac leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are many other reasons why removal of an inoperable lead may be desirable. For example, if there are too many leads positioned in a vein, the vein can be obstructed to the extent that fluid flow through the vein is compromised. In addition, multiple leads can be incompatible with one another, thereby interfering with the pacing or defibrillating function. An inoperable lead can migrate during introduction of an adjacent second lead, and mechanically induce ventricular arrhythmia. Other potentially life-threatening complications can require the removal of the lead as well. For example, removal of an infected cardiac lead may be desirable so as to avoid conditions such as septicemia or endocarditis. Finally, such removable may be desirable so that the space occupied by the inoperable lead in the vein could be better utilized, e.g., by the presence of a new lead.

Surgical removal of a heart lead in such circumstances may require open heart surgery. However, open heart surgery is accompanied by significant risk and cost to the patient, as well as a potential for unintended complications. A variety of methods and apparatuses have been devised as alternatives to open heart surgery for heart lead removal. Several of these methods and apparatuses are described in related patents and publications, such as U.S. Pat. No. 5,697,936, titled "Device for Removing an Elongated Structure Implanted in Biological Tissue"; U.S. Pat. No. 5,507,751, titled "Locally Flexible Dilator Sheath"; U.S. Pat. No. 5,632,749, titled "Apparatus for Removing an Elongated Structure Implanted in Biological Tissue"; U.S. Pat. No. 5,207,683, titled "Apparatus for Removing an Elongated Structure Implanted in Biological Tissue"; U.S. Pat. No. 4,943,289, titled "Apparatus for Removing an Elongated Structure Implanted in Biological Tissue"; U.S. Pat. No. 5,011,482, titled "Apparatus for Removing an Elongated Structure Implanted in Biological Tissue"; U.S. Pat. No. 5,013,310, titled "Method and Apparatus for Removing an Implanted Pacemaker Lead"; U.S. Pat. No. 4,988,347, titled "Method and Apparatus for Separating a Coiled Structure from Biological Tissue"; U.S. Pat. No. 5,423,806, titled "Laser Extractor for an Implanted Object"; U.S. Pat. No. 6,419,974, titled "Radio Frequency Dilator Sheath", U.S. Pat. Nos. 6,687,548 and 6,712,826, each titled "Apparatus for Removing an Elongated Structure Implanted in Biological Tissue"; U.S. Patent Publ. No. 2006/0235431, titled "Lead Extraction Device'" U.S. Patent Publ. No. 2006/0253179, titled "Tip for Lead Extraction Device"; U.S. Patent Publ. No. 2008/0071341, titled "Tip for Lead Extraction Device"; and U.S. Patent Publ. No. 2008/0071342, titled "Vessel Entry Device"; among others. Each of the aforementioned patents and patent publications is incorporated by reference as if fully set forth herein.

Many of the aforementioned patents and patent publications describe manual, or mechanical, devices that are used for removing an implanted structure, such as a cardiac lead. Others describe non-mechanical techniques, such as laser extraction and radio frequency extraction. Although the prior art devices have been found to be reasonably effective in many situations, physicians continue to encounter particularly challenging situations in which existing extraction devices may not provide satisfactory or consistent results. Due to the multiplicity of factors that may contribute to the difficulty in extracting an implanted lead, a technique that may be effective in one instance may not provide similarly successful results in another instance.

For example, manual devices normally are provided with a single rotating flexible sheath, or dual telescoping flexible sheaths, for tracking over the cardiac lead. Such sheaths are generally formed from a polymer, and have the flexibility to enable the sheath to traverse tortuous pathways in the vessel. However, such rotating sheaths may lack sufficient strength to cut through particularly tough tissue growth and calcification around the implanted lead. On some occasions, such devices are provided with a metallic tip at the distal end of the sheath, or at the distal end of the inner sheath in the dual sheath arrangement. As described in the incorporated-by-reference U.S. Patent Publication Nos. 2006/0253179, 2008/

0071341, and 2008/0071342, the tip may include a generally helical or like structure protruding radially from the outer surface of the tip. Among other things, the radial protrusion often improves the ability of the tip to core or otherwise non-cuttingly disrupt the encapsulating tissue from the lead as the rotating sheath and tip advance through the vessel. However, on some occasions, the presence of a radial protrusion along the outer surface of the tip may promote lead wrap; e.g., the undesired wrapping of another implanted lead in the vessel around the rotating tip or around the implanted lead targeted for removal.

Laser and radio frequency devices normally utilize metallic sheaths. Such sheaths typically provide a good deal of strength to enable the sheath to cut through fibrous growths. However, some growths are resistant to metallic sheaths. In addition, these sheaths may lack the flexibility desired to maneuver tortuous pathways. Laser and radio frequency systems can also be expensive, particularly when compared to mechanical devices. Further, many facilities lack the equipment necessary to carry out these techniques.

It would be desirable to provide a device and tip structure that is effective for removing implanted leads from a vessel, that is easy to operate, and that is versatile enough to overcome many of the obstacles that may be encountered in such operations with existing devices.

BRIEF SUMMARY

The present invention addresses the problems of the prior art extraction devices. In one form thereof, the invention comprises a tip engageable with an elongated sheath for extracting an implanted structure from an obstruction in a body vessel of a patient. The elongated sheath has a distal end and a passageway extending at least substantially therethrough. The tip comprises a tip body having a proximal portion, a distal portion, a substantially flat leading face, and a passageway extending therethrough. The tip body proximal portion is engageable with the sheath distal end, and the respective passageways are dimensioned and aligned such that the implanted structure is receivable therein. The tip body distal portion comprises a plurality of sides extending circumferentially therearound. The sides have respective ends and an inwardly directed radiused portion between adjacent ends.

In another form thereof, the invention comprises a device for extracting an elongated implanted structure from an obstruction within a vessel of a patient. An elongated sheath has a distal end, and a passageway extending therethrough. The sheath is sufficiently flexible to track over the implanted structure within the vessel. A tip has a proximal portion, a distal portion, a substantially flat leading face, and a passageway extending therethrough. The tip proximal portion is engageable with the sheath distal end such that the passageways are aligned to receive the implanted structure therein. The tip distal portion has an outer diameter substantially the same as the outer diameter of the elongated sheath, and has an axial length of between about 0.030 and 0.070 inch. The tip distal portion comprises between about 7 and 13 sides extending circumferentially therearound. Each of the sides has respective ends and an inwardly directed radiused potion between adjacent ends. Each end is aligned to intersect with the substantially flat leading face to define a point configured to facilitate disruption of the implanted structure from the obstruction upon a rotation of the device.

In yet another form thereof, the invention comprises a tip engageable with an elongated sheath for providing access to an interior of a vessel through an opening in a wall of the vessel for removing an elongated indwelling structure therefrom. The elongated sheath has a distal end and a passageway extending at least substantially therethrough. The tip comprises a tip body having a proximal portion, a distal portion, and a passageway extending therethrough. The tip body proximal portion is engageable with the sheath distal end, and the respective passageways are dimensioned and aligned such that the implanted structure is receivable therein. The tip body distal portion comprises a plurality of sides extending circumferentially therearound. The sides have respective ends, and a first radiused portion R1 inwardly directed between adjacent ends. The ends axially extend in a distal direction beyond a distal face of the tip body to respective distal points. A second radiused portion R2 is inwardly directed between adjacent points.

BRIEF DESCRIPTION OF THE DRAWINGS

FIG. 4 is a view showing the handle and sheath of the lead extraction device prior to assembly;

FIG. 5 is a view of the reverse side of an embodiment of a lead extraction device including a power supply;

DETAILED DESCRIPTION OF THE DRAWINGS AND THE PRESENTLY PREFERRED EMBODIMENTS

Figure 1:
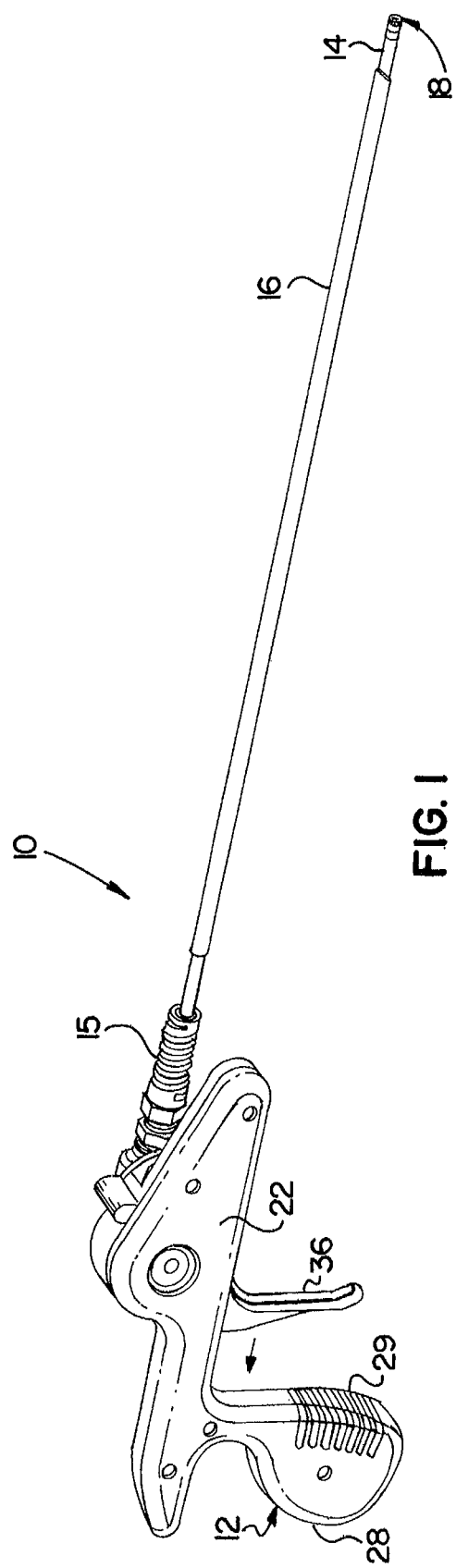
FIG. 1 is a perspective view of an embodiment of a lead extraction device of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component) that is at the greatest distance from the operator, or that is initially inserted into the patient.

The implanted elongated structure targeted for removal may comprise a cardiac lead. A cardiac lead, as the term is used herein, refers to a lead that is used in connection with a heart-related device. Non-limiting examples of cardiac leads that may be extracted by the inventive device include pacemaker leads, defibrillator leads, coronary sinus leads, and left ventricular pacing leads. When the device is used to remove a cardiac pacemaker lead, the distal end of the cardiac lead will normally be located within the vascular system of the patient, and in particular, within a chamber of the patient's heart (such as in an atrium or ventricle of the heart). When the implanted elongated structure is a defibrillator lead, the distal end of the structure may be located either in or about the heart of the patient. The distal ends of other types of implanted elongated structures targeted for removal may not necessarily be near the heart.

In addition to cardiac leads, the invention may also be used in the removal of other elongated structures or leads, such as neurological pacing and stimulation leads. A non-limiting list of still other structures that can be removed by the inventive device includes implanted catheters, sheaths, cannulae and the like. For convenience, the following discussion will refer to the removal of a cardiac lead, such as a pacemaker or a defibrillator lead. However it should be understood that this is not intended to be a limitation on the scope of the invention, and that the device may be suitable for removal of other elongated structures, such as the structures referred to above.

Typically, a cardiac lead comprises an inner core, comprising a cable or a coil, surrounded by a layer of insulating material. Some cardiac leads have a lumen extending therethrough, while others (i.e., "lumenless" leads) do not. The extraction devices of the present invention are useful for extracting implanted leads having a lumen, as well as lumenless leads. When an inventive device is to be used for removal of a cardiac lead, those skilled in the art will appreciate that the lead should initially be severed from the control device, such as the pacemaker or defibrillator, prior to any attempts to remove the lead. Since the control device will normally have a much larger diameter than the remainder of the lead, only an unreasonably large dilator sheath could fit over the control device.

FIG. 1 is a perspective view of an embodiment of a lead extraction device 10 for use in separating an elongated structure, such as a cardiac electrical lead, from encapsulating biological tissue. When a cardiac lead is implanted in a vessel, all or a portion of the elongated structure of the lead may become encapsulated over time by fibrotic biological tissue that grows against the wall of the vessel or surrounding tissue. The inventive lead extraction device 10 is particularly useful for removing the encapsulated cardiac lead from the vein of a patient. In the embodiment shown, lead extraction device 10 comprises a handle 12, inner and outer coaxial sheaths 14, 16 extending distally from handle 12, and a tip 18 at a distal end of the inner sheath 14. As shown in the figure, an optional strain relief 15 may be provided at the proximal end of sheath 14 to inhibit kinking of the sheath.

Although handle 12 and outer sheath 16 are shown in this embodiment, these features are optional and need not be included in all instances. Many users may find the handle to be convenient in providing rotary action to the sheath. However, other users may prefer to manually rotate and/or advance the sheath 14 into the vessel. Therefore, lead extraction device 10 may, or may not, include a handle. When present, outer sheath member 16 is typically free floating in the device, or in other words, is not affixed to other portions of the device. Although optional, the presence of an outer sheath 16 that covers a majority of the length of the inner sheath 14 as shown is generally preferred. The presence of the outer sheath can inhibit other objects, such as other indwelling devices (other pacing leads, etc.), from interfering with the inner sheath as the inner sheath rotates. The outer sheath can also aid in dilating the vessel entry site to allow for smoother entry and reentry of subsequent extraction devices. In addition, if the primary lead anchoring location is at the vessel entry site, the lead may readily slide out once the device gains vessel access. In this instance, the outer sheath functions as a conduit in allowing the lead to be drawn past tortuous regions (such as the tight clavicular region), and out of the body.

Figure 2:
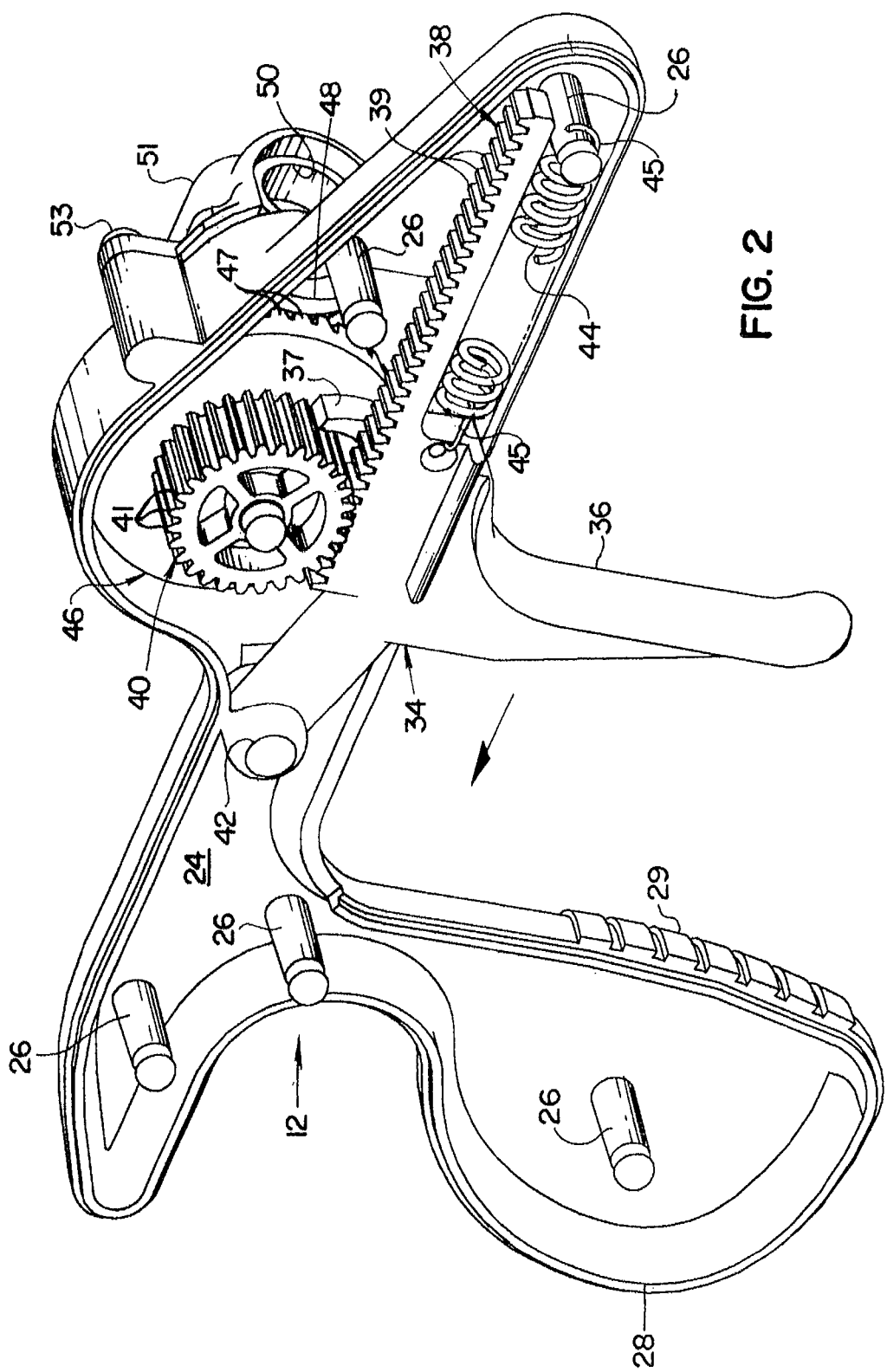
FIG. 2 is a perspective view of the handle of the lead extraction device of FIG. 1, with a portion of the outer wall removed to illustrate the inner components of the handle.

In the embodiment shown, handle 12 includes opposing handle walls 22, 24. FIG. 2 is a perspective view of handle 12 wherein handle outer wall 22 has been removed to provide visualization of the internal workings of this handle. Handle walls 22, 24 are connected via a snap fit or other conventional mechanism. In the embodiment shown, handle wall 24 includes a plurality of transverse pegs 26 that are received in corresponding receptacles (not shown) in handle wall 22. Handle 12 may be provided with an ergonomically shaped grip 28, as shown in the figures. If desired, ergonomic grip 28 may also include a plurality of ribs 29 spaced along a hand-engaging surface of grip 28.

Handle 12 includes a translation mechanism 34. Translation mechanism 34 utilizes a rack and gear structure to translate linear motion generated upon pull of an actuator, such as trigger 36, into rotational motion of inner sheath 14. Translation mechanism 34 includes a rack 38 having a plurality of teeth 39 as shown. Rack 38 is engaged with trigger 36, such that upon the operator pulling trigger 36 in the proximal direction (as indicated by the arrow in FIG. 2), rack 38 likewise is urged linearly in the proximal direction.

An external spur gear 40, having a plurality of teeth 41, is aligned with rack 38 such that spur gear teeth 41 mesh with rack teeth 39. Linear movement of rack teeth 29 causes spur gear 40, and thus teeth 41, to rotate in the direction shown. A pawl 37 may be provided to inhibit undesired (counter-clockwise) rotation of the spur gear. If desired, pawl 37 may also be configured to create ratcheting action upon movement of rack 38 and spur gear 40, and to provide an audible confirmation of the rotation of the spur gear. A stabilizing arm 42 extending in a proximal direction from rack 38 may be provided to maintain proper orientation of rack 38 in handle 12, and to ensure smooth movement of the trigger without bending or flexing when pulled under a load. Preferably, a spring 44 is affixed at one end to rack 38 and at the other end to housing wall peg 26 (distal of rack 38), for urging trigger 36 back to the position shown in FIG. 2 upon relaxation of the tension resulting from the trigger pull by the operator. Spring 44 may be retained in handle 12 by any conventional means, such as hooks 45.

Spur gear 40 is affixed to large bevel gear 46, in a manner such that rotation of spur gear 40 causes a corresponding rotation of large bevel gear 46. Large bevel gear 46 includes a plurality of teeth 47 on a side of large bevel gear 46 opposite spur gear 40. A small bevel gear 48 is rotationally aligned with large bevel gear 46 in conventional fashion, such that large bevel gear teeth 47 mesh with small bevel gear teeth (not shown). The large and small bevel gears are aligned in conventional fashion for such bevel gears, e.g., at an angle of about 90 degrees. As a result, the direction of rotation is translated via said gears along the 90 degree angle.

A hub 50 is affixed to small bevel gear 48 for rotation in accordance with the rotation of the small bevel gear. Hub 50 is sized and shaped to securely receive a proximal end of inner sheath 14, by conventional means such as adhesion, friction and/or threading. Sheath 14 is preferably engaged with the hub 50 in a manner such that it may be selectively affixed to, or removed from, the hub. Further description of the handle is provided in incorporated-by-reference U.S. Patent Publication 2006/0253179.

Figure 3:
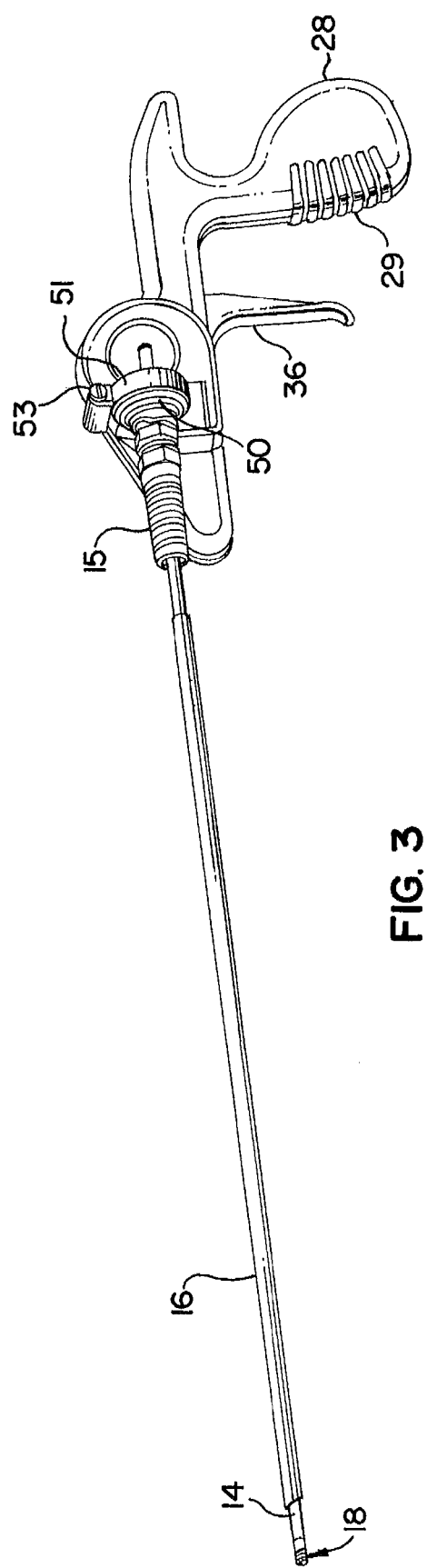
FIG. 3 is a side view of the opposite side of the lead extraction device shown in FIG. 1.

FIG. 4 illustrates one preferred manner in which sheath 14 may be removably affixed in device 10. In this figure, optional outer sheath 16 has been omitted. Handle wall 24 includes a pivotable wall portion 51 that may be pivoted to the open position as shown in the figure. Sheath 14 is provided with a flange 17 at the proximal end of the sheath, to seat the sheath in the hub. When the sheath is affixed in hub 50, flange 17 is snugly received against a surface 52 of pivotable portion 51. When portion 51 is pivoted into the closed position, a conventional latching mechanism, such as a screw 53 is provided to maintain pivotable portion 51 in the closed position shown in FIG. 3, thereby retaining sheath 14 in handle 12. Those skilled in the art will appreciate that there are numerous other ways in which the sheath may be held in the device, and that the particular removable affixation mechanism described herein is not crucial to the invention.

Thus, as has been shown, sheath 14 may be selectively attached to, and detached from, handle 12. In this manner, sheath 14 and tip 18 may simply be removed from handle 12 following a lead extraction procedure, and replaced with another sheath and tip for use in a subsequent procedure. Similarly, by utilizing detachable components, sheath 14 and tip 18 may be removed and replaced with a sheath and tip of a larger, or smaller, size (length and/or diameter) as may be appropriate for removal of a particular lead. Those skilled in the art will appreciate that the device can likewise be structured such that the sheath and tip are permanently affixed in the device. In this event, the device may be discarded following use.

During manual operation of device 10 shown in FIGS. 1-4, the operator pulls trigger 36 in the linear direction shown. As discussed, this action drives, or translates, the linear motion of the trigger pull to rotary movement of hub 50, thereby causing rotation of sheath 14. The remaining features of the translation mechanism not described herein are conventional, and need not be further explained or illustrated to enable one skilled in the art to utilize the mechanism for the purposes described.

Rack and gear structures are well known in the art, and the specific structure described and shown herein is not intended to represent the only way that such translation can be accomplished. Those skilled in the art will appreciate that there are numerous other ways in which a manual device can be structured such that an action generated by an operator, such as the trigger pull described herein, may result in rotary motion. All such techniques within the knowledge of one skilled in the art are considered within the scope of the invention.

FIG. 5 illustrates another feature of the invention. In this embodiment, the rack and gear structure, as well as the trigger of FIGS. 1-4, have been eliminated. These features have been replaced with a power source, such as drive motor 54. The power source may comprise any conventional source suitable for driving the rotation of the hub, such as a source for generating electrical, battery or pneumatic power. A suitable actuator, such as button 55, may be provided to selectively activate, and deactivate, drive motor 54. Upon actuation, the drive motor operates in well known fashion to cause sheath 14 to rotate.

Although the translational mechanism and trigger have been removed from the embodiment shown in FIG. 5, this need not be the case. Rather, device 10 can be provided with both a manual operation (such as via trigger 36 and translation mechanism 34) and a powered operation (such as via drive motor 54). In this case an operator can selectively utilize either, or both, of these features during a particular lead extraction procedure.

Sheaths 14, 16 may be formed from conventional biocompatible materials well known for such purposes in the medical arts. Polymeric materials such polypropylene, polyurethane, polyethylene, nylon, PTFE, and the like, are believed to be particularly appropriate. As stated above, extraction devices typically comprise an inner sheath 14 as described having the tip engaged at the distal end of the sheath, and a telescoping outer sheath 16. If desired, either sheath can be reinforced with a coil or with a braided material. Such reinforcements are well known in the medical arts, and are typically formed from a metal or metal alloy, or from a composite material. The compositions described hereinabove are exemplary, and those skilled in the art will appreciate that other compositions may be substituted, such substitutions being within the scope of the invention.

A sheath for use in a device for removing an implanted elongated structure, such as a cardiac lead, should have a length and flexibility such that it is capable of extending through enough of the body vessel to at least partially free the cardiac lead from the endothelial growth. For best results, the device will be structured such that torque can be transmitted by the operator from the proximal end of the inner sheath to the distal tip. In this manner, the operator need merely insert the sheath into the vessel, and thereafter direct, or torque, the sheath to the desired site to enable the tip to core or otherwise non-cuttingly disrupt the growth encapsulating the lead.

As stated, tip 18 is secured to the distal end of inner sheath 14. Tips suitable for use herein may be fabricated by known techniques, such as machining and metal injection molding, from materials having sufficient strength and rigidity to advance through or otherwise disrupt obstructions encountered during removal of the elongated implanted structure. Metals and metal alloys, such as stainless steel, nitinol and titanium, are particularly preferred tip materials. Those skilled in the art will appreciate that other compatible materials may be used in place of metal or metal alloys. For example, the tip may alternatively be formed from a fiber-reinforced polymer, such as fiber-reinforced polypropylene. Non-limiting examples of suitable fiber reinforcements include glass and carbon fibers. In one embodiment, the tip may be formed of a polymer, such as polypropylene, and may be molded or bonded onto the end of a sheath formed from a polymer that is compatible with the polymer of the tip material. In most cases, it is preferred to provide a tip formed of a composition having greater strength and/or hardness than the sheath, so that the tip is better able to core or otherwise disrupt the endothelial growth.

Distal tips for lead extraction devices are known in the art. Although many such tips are effective in some instances, those same tips may be either partly or wholly ineffective in other instances. For example, some tips have cutting and/or disrupting protrusions extending outwardly from the outer surface of the tip. Examples of disrupting tips are provided in the incorporated-by-reference U.S. Patent Publ. Nos. 2006/0253179 and 2008/0071341. Some of these tips have radial, helical-like protrusions disposed along the outer surface of a portion of the tip. These tips have been found to be very effective in some situations, as the radial helical protrusion improves the ability of the tip to core or otherwise non-cuttingly disrupt the encapsulating tissue from the lead during rotation of the sheath and tip. However, the tips have been less effective in other situations. For example, when the vessel includes a plurality of leads, the presence of the radial protrusion along the outer surface of the tip provides a surface that may promote lead wrap in some instances. Lead wrap refers to the undesired wrapping of another implanted lead in the vessel around the rotating distal tip, or around a target lead, during extraction of the target lead. In most instances, it is desired to maintain the "wrapped" lead in the vessel, and the undesired wrapping can cause breakage of the wrapped lead, or other unintended consequences in the vessel. Thus, lead wrapping is normally undesired, and should be minimized to the extent possible.

Figure 6:
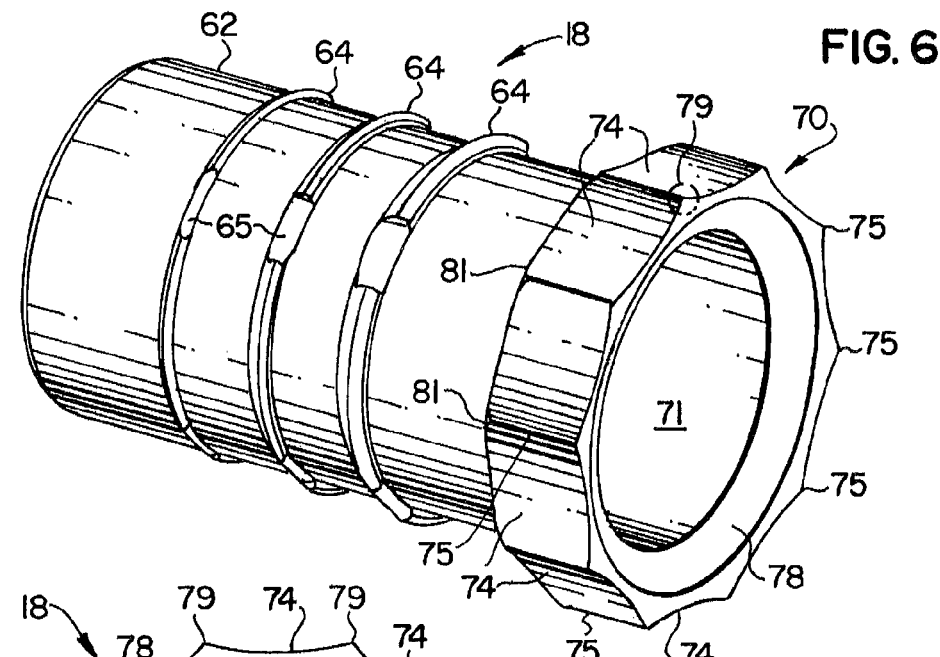
FIG. 6 is an enlarged perspective view of one embodiment of a distal tip for a lead extraction device.

FIG. 6 is an enlarged perspective view of one embodiment of a distal tip 18. Distal tip 18 may be joined to the distal end of a device, such as the sheath of a lead extraction device as described herein. Typically, the distal tip is bonded, adhered, or otherwise affixed to the distal end of a sheath in a secure manner, such that the tip will not disengage from the sheath under normal conditions encountered during use.

Figure 7:
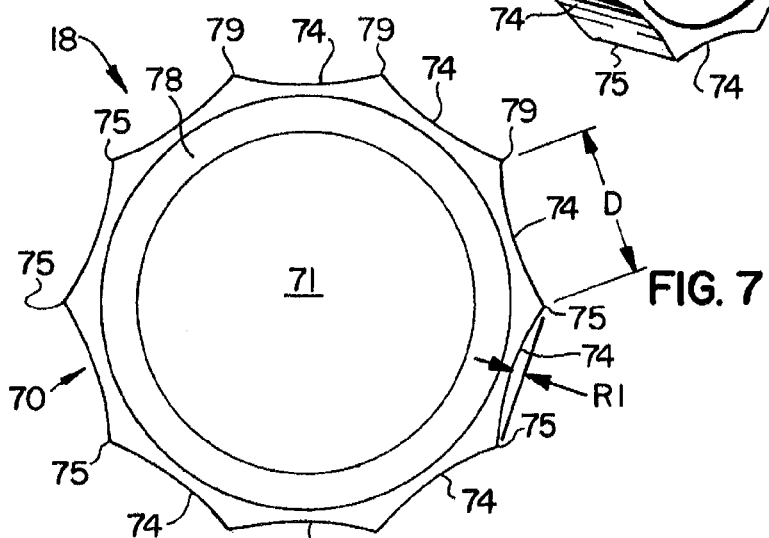
FIG. 7 is an end view of the tip of FIG. 6 as viewed from the distal end of the tip.
Figure 8:
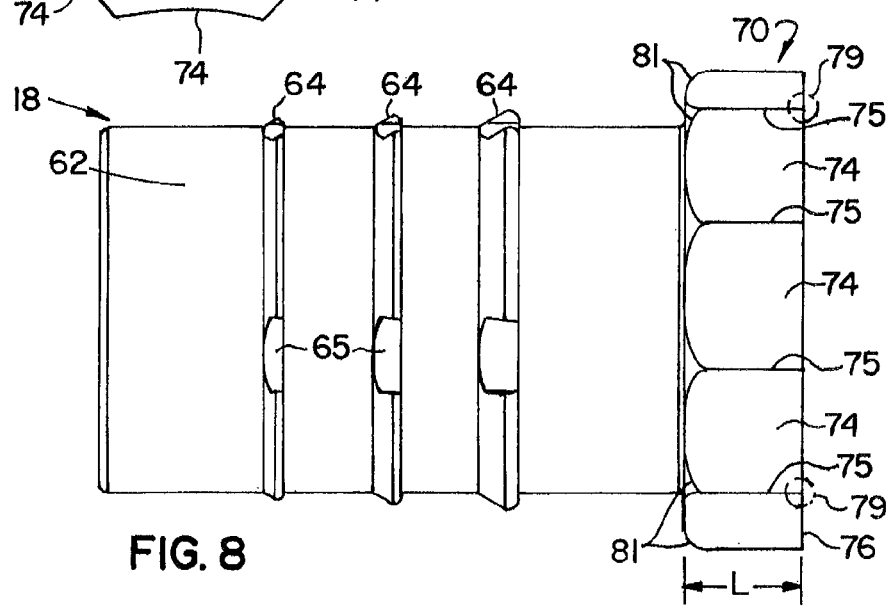
FIG. 8 is a side view of the tip of FIG. 6.

FIG. 7 is an end view of tip 18, as viewed from beyond the distal end of the tip. FIG. 8 is a side view of tip 18. In the non-limiting embodiment shown, tip 18 has a smaller diameter proximal portion 62 and a larger diameter distal portion 70. A passageway 71 extends through tip 18, such that when the tip is affixed to the distal end of inner sheath 14, passageway 71 is aligned with the passageway extending through the sheath to enable passage therethrough of the implanted structure, e.g., the cardiac lead.

Smaller diameter proximal portion 62 of the tip 18 may be received in, and affixed to, the inner surface at the distal end of the sheath, such as sheath 14. The ring may include attachment members, such as rings 64, to enhance the engagement between the tip and the sheath. As shown in the figures, proximal tip portion 62 may include one or more rings 64 fitted along the outer surface of proximal portion 62. In the embodiment shown, a plurality of rings 64 are aligned enhance the engagement between proximal tip portion 62 and the interior surface of sheath 14. When more than one ring is present, rings 64 are preferably aligned in order of increasing width of the ring body in the direction of the distal tip.

Providing rings having a smaller width in the proximal direction minimizes the stresses in the sheath at the area of joinder of the sheath and the tip, where stresses resulting from tension, torsion, and bending tend to be the highest. If desired, rings 64 may be provided with one or more cut-outs 65. Cut-outs 65 serve to inhibit relative rotation between the tip and the sheath when the proximal tip portion is positioned inside the distal portion of the sheath. Rings 64 are further described in the incorporated-by-reference U.S. Patent Publ. Nos. 2006/0253179 and 2008/0071341.

Although the embodiment illustrated in FIG. 6 comprises rings 64 for engagement with the inner surface of sheath 14, those skilled in the art will appreciate that other conventional attachment mechanisms may be substituted in a particular case. For example, rather than rings, the proximal end of tip 18 can be provided with one or more barbs positioned along the proximal length of the tip, which barbs are configured to attach to the inner surface of the sheath. As another alternative, the proximal end of tip 18 can be adhered to the inner surface of the sheath with a suitable adhesive. To enhance adhesion, tip proximal portion 62 may be provided with a roughened outer surface, e.g., by bead blasting and/or etching of the surface.

In other embodiments, the proximal portion of the tip need not have a smaller diameter than the distal portion. Those skilled in the art will appreciate that other common means of securely affixing a distal tip to the distal end of a device, such as the sheath described herein, can be substituted, and such engagement need not result from receipt of a smaller diameter proximal portion in larger diameter sheath.

As stated, an embodiment of tip 18 as illustrated herein includes a larger diameter distal portion 70. Preferably, when the proximal end 62 of the tip is received in inner sheath 14 as shown, e.g., in FIG. 1, the outer diameter of tip distal portion 70 is substantially the same as the outer diameter of sheath 14. Although this arrangement is preferred, it is not critical, as those skilled in the art will appreciate that other diameters are suitable in a particular instance.

The tip will now be described with reference to one preferred embodiment, namely the ten-sided tip shown in FIGS. 6-8. Those skilled in the art will appreciate that this illustrated embodiment represents only one possible tip configuration, and that other configurations may be substituted for a particular application within the scope of the invention.

In the non-limiting embodiment shown, distal portion 70 has ten sides 74. As best shown in FIG. 7, each of the ten sides comprises two ends 75, and an inwardly directed radiused portion between the two ends. Since the ten sides are sequentially disposed around the circumference of the tip distal portion in this embodiment, each end 75 will comprise an end for two adjacent sides 74. Preferably, each end 75 comprises a relatively sharp radially outwardly directed edge as shown. Providing a sharp edge as described enhances the ability of the tip to advance along the encapsulated lead. Since the outer diameter of the tip will not typically exceed the outer diameter of the sheath 14, as discussed above, the sharp edges do not extend in the radial direction a distance that might otherwise cause damage to the vessel. Although less desired, an end can alternatively comprise a relatively short flattened portion between adjacent sides 74.

Although tip 18 is shown having ten sides, this is merely one example. Those skilled in the art will appreciate that the possible number of sides may vary. Preferably, tips for use herein may have anywhere between five and fifteen sides. In some embodiments, the tip may have between seven and thirteen sides, and in still other embodiments, the tip may have between eight and twelve sides, or between nine and eleven sides. In the presently preferred embodiment, however, the tip has ten sides as described above.

It is believed that those skilled in the art can readily fashion a tip having a suitable number of sides without undue experimentation. Generally speaking, providing too few sides to the tip may create a paddle-like situation, which may provide sufficient surface area along the tip circumference to promote lead wrapping. On the other hand, providing too many sides could effectively transform the outer circumference of the distal tip portion into a cylindrical-like surface, thereby effectively eliminating the radii along the respective sides 74.

Although not required, in one preferred embodiment all sides 74 are substantially identical in length and depth (radii). A distance D (FIG. 7) between adjacent ends 75 may be about 0.060 to 0.070 inch along the circumference of the tip, such as about 0.063 inch. By providing a tip having identical, or substantially identical sides, the tip 18 can be bi-rotational, i.e., it can be rotated in either direction if desired. Although typically a tip will only be rotated in a single direction, there may be some instances in which a bi-rotational tip is desired. For example, in instances in which lead wrap is a concern, it can be advantageous to have a capability to rotate the tip in both directions. By incorporating a reciprocating back and forth type rotation, the lead never proceeds far enough in one direction to allow it to wrap around the tip and/or the sheath. In other embodiments, the sides need not necessarily have substantially identical length and/or depth.

The presence of the inwardly-directed radius along the respective sides 74 of the tip enhances the ability of the tip to embed in the tissue by reducing the overall wall thickness of this portion of the tip. By decreasing the surface area of the leading face of the tip that makes initial contact with the tissue, the presence of the radius presents a receiving surface along the respective sides 74 that allows the tissue to embed (sag) into these semi-recessed surfaces (radii) of the respective sides 74. Only a small amount of sag is normally desirable to disrupt and separate the tissue.

The radius preferably extends radially inwardly a distance R1 (FIG. 7) of between about 0.006 and 0.012 inch, and more preferably between about 0.008 and 0.010 inch, measured from an axial midpoint between respective ends 75. Those skilled in the art will recognize that this distance R1 may vary depending upon the maximum outer diameter of the tip portion 70, and may be greater or lesser than the distance R1 recited above.

The presence of the radius along the respective sides 74 thus provides a lower profile and a less aggressive leading face when compared to tips having protrusions that extend radially outwardly beyond the diameter of the sheath. As a result, the tip is able to engage the tissue and/or an adjoining structure (e.g., another lead in the vessel). However, since the tip does not typically extend radially outwardly beyond the outer diameter of the inner sheath 14, the tip structure does not provide a surface that would cause the lead to wrap or grab the tissue or an adjoining structure, such as an adjacent lead. In addition, the tip would not interfere with the free movement of the outer sheath 16 (when present).

Those skilled in the art will appreciate that providing only a minimal inward radius may reduce the ability of the tip to embed and disrupt the tissue, and instead, could result in the tip having a "sit and spin" scenario. Similarly, providing an extreme inward radius may result in such a thin-walled tip (measured between the radius inner diameter and the inner diameter of the tip) that the tip has a sharp leading face. When present, a sharp leading face may cause the tip to embed deeply into the tissue upon initial contact. In this event, further rotation of the tip may cause the tip to hold onto the tissue, such that the tissue rotates with the tip instead of disrupting it, thereby possibly resulting in lead wrap whereby the tissue rotates with the tip, instead of being disrupted by the tip.

The embodiment of distal portion 70 shown in FIGS. 6-8 is preferably provided with a flat leading face 76. The flat leading face is best shown in FIG. 8. A radiused inner circumferential edge 78 leads from the flat leading face to inner passageway 71. The radiused inner edge is best shown in FIG. 6. Although not required, the presence of the flat leading face 76 and radiused inner edge 78 are provided in this embodiment to protect the tracked lead from being cut or damaged when rounding a bend.

When respective ends 75 are sharp edges as described and shown, e.g., in FIG. 7, the intersection of the flat leading face and the sharp edges 75 defines a plurality of relatively sharp points 79. The number of points 79 will thus be the same as the number of sharp ends, or edges, 75. By providing relatively sharp points 79 along the leading face of the tip, the tip is better able to engage the encapsulating tissue when rotation is applied. The points react directly upon the tissue without cutting the lead and/or the vessel wall, since action to free the implanted structure is taking place at the very corner of the tip, and not on its face or side.

The tip embodiment as shown and described in FIGS. 6-8 does not have a leading (i.e., axial) cutting element, in the nature of a hole saw or similar structure, that is sometimes provided to cut an obstruction upon contact. Rather, the tip 18 is structured to disrupt the encapsulating tissue from the cardiac lead through force and rotation as it advances through the vessel. Although in some embodiments minimal irregularities (e.g., pitted leading end, etc) can be provided along the leading face of the tip, such irregularities will not constitute a cutting face in the nature of a hole saw or like structure. As described herein, the outer diameter configuration and the points 79 work in tandem to perform a precise corner directed separation of the tissue from the lead. When rotational force is applied, the tip thereby incorporates precision disruption to achieve tissue separation.

As best shown in FIG. 8, distal portion 70 of the tip will preferably have a curved trailing surface 81. Providing a curved trailing surface facilitates withdrawal of the device from the vessel by eliminating sharp corners on the trailing surface. By eliminating sharp corners on the trailing end, the likelihood that the tip will grab or otherwise snag tissue or adjoining structures in the vessel upon withdrawal is minimized.

The following dimensions relate to one preferred embodiment of a tip. This embodiment comprises a ten-sided tip as described and shown in FIGS. 6-8. The overall length of the tip is conventional, e.g., about 0.300 inch. With conventional tips, the length of the larger diameter distal portion typically comprises about 0.125 inch, with the proximal portion comprising the remaining 0.175 inch. However, in the inventive tip described herein, larger diameter distal portion length L (FIG. 8) is less than that of conventional tips, e.g., preferably between about 0.030 and 0.070 inch, and more preferably about 0.050 inch. By providing a tip with a shorter distal length L than in conventional tips, less longitudinal surface is provided for undesired wrapping or grabbing by tissue in the vessel or adjoining structures in the vessel. As stated above, the radius preferably extends radially inwardly a distance R1 (FIG. 7) of between about 0.006 and 0.012 inch, and more preferably between about 0.008 and 0.010 inch.

Figure 9:
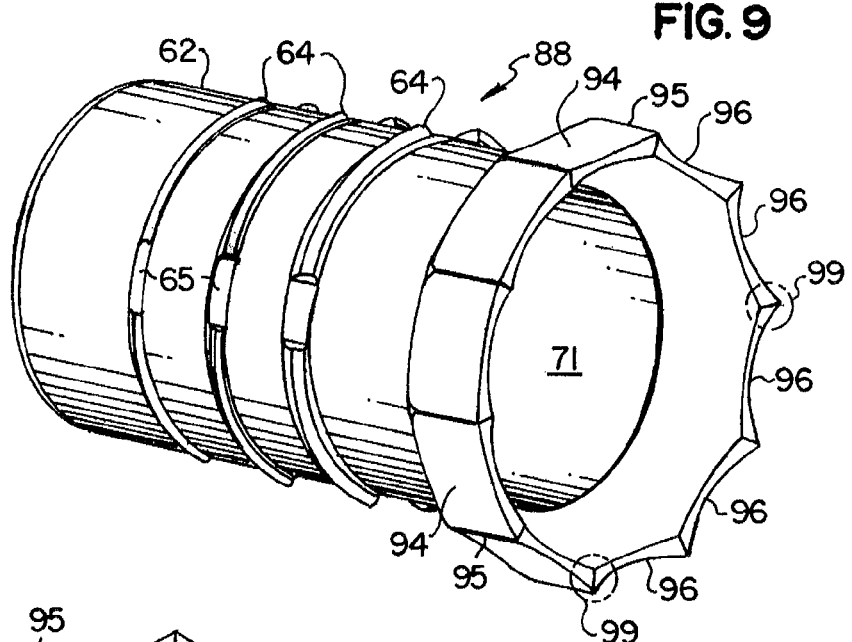
FIG. 9 is an enlarged perspective view of another embodiment of a tip.
Figure 10:
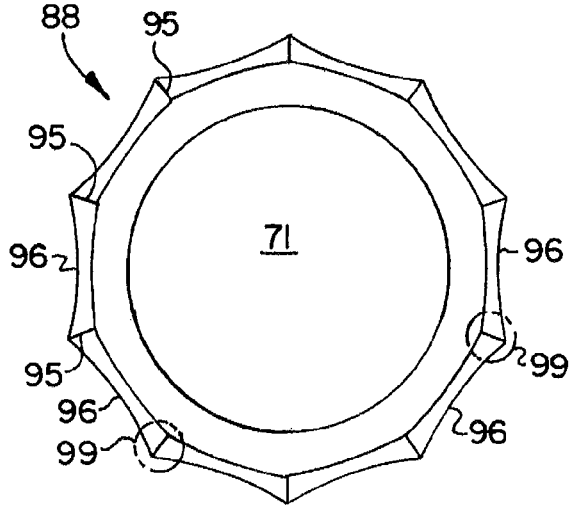
FIG. 10 is an end view of the tip of FIG. 9, as viewed from the distal end of the tip.
Figure 11:
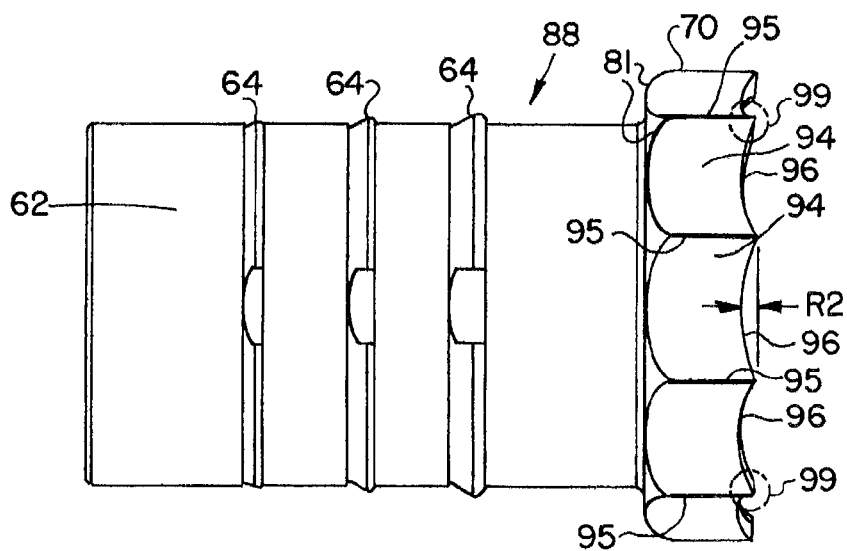
FIG. 11 is a side view of the tip of FIG. 9.

Another embodiment of a tip 88 is shown in FIGS. 9-11. FIG. 9 is an enlarged perspective view of tip 88. FIG. 10 is an end view of tip 88 as viewed from beyond the distal end of the tip, and FIG. 11 is a side view of tip 88. Where appropriate, the reference numerals used in FIGS. 6-8 have been retained in FIGS. 9-11 to indicate the same elements in each embodiment. Tip 88 will have many features, and dimensions, in common with tip 18. Unless otherwise specified herein, the skilled artisan will appreciate that these previously-described features, and dimensions, of tip 18 may also be utilized for tip 88.

Unlike the flat leading face 76 of tip 18 (FIGS. 6-8), tip 88 is provided with a more aggressive leading face. Although a flat leading face is generally preferred when the tip is used for freeing a lead from encapsulating tissue along a body vessel as described hereinabove, this tip structure may be less effective for other uses, such as during initial entry through the vessel wall. In this instance, a more aggressive leading face is often desirable to enable the lead to cut through the vessel wall.

A device for initial entry through a vessel wall is disclosed in the incorporated-by-reference U.S. Patent Publ. No. 2008/0071342, titled "Vessel Entry Device". As described in the publication, an end of an implanted structure, such as a cardiac lead, intended for extraction is typically severed from the pacemaker or other device such that the free end of the lead protrudes through the vessel. Typically, the vessel opening through which the cardiac lead passes has closed around the lead with the passage of time, and scar tissue and/or calcifications may have formed at that point. The vessel entry device is placed over the free (severed) end of the lead, and advanced toward the calcified vessel opening.

For initial vessel entry of calcified openings, less aggressive leading ends, such as the leading end of tip 18, may not be sufficient for entry through the vessel. In such cases, a more aggressive tip may be utilized to cut though the calcified vessel opening in a manner that frees the lead from the obstructions, and permits entry of an extraction device into the vessel.

During initial vessel entry, it is also generally desirable to utilize a sheath having a lesser length, and a greater rigidity, than a sheath utilized in extracting the lead from obstructions encountered within the vessel. During vessel entry, a more flexible lead extraction device cannot generally be pushed through the calcified opening, at least not without the necessity for the physician to exert an undesirable amount of pushing force. Thus, with a more rigid and shorter sheath, and a tip having a more aggressive leading end, less force will typically need to be expended by the physician to penetrate the scar tissue, etc. Tip 88 is particularly suitable for such use. Further discussion of the considerations encountered during vessel entry are discussed in the incorporated-by-reference U.S. Patent Publ. No. 2008/0071342.

Tip 88 may include a proximal portion 62 having attachment members, such as the rings 64 in the embodiment of FIGS. 6-8. In large part, many dimensions of tip 88 may be the same as, or similar to, those of tip 18 as described previously.

As best shown in FIGS. 9 and 11, tip 88 is structured such that a series of radii 96 is defined at the leading (distal) face of tip 88. In this case, each one of the ten (for example) sides comprises two ends 95, in the same manner as ends 75 of tip 18. However, unlike ends 75 in the embodiment of FIGS. 6-8 that terminate at flat face 76, ends 95 extend axially in the distal direction to respective points 99. Once again, the number of points 99 will be the same as the number of sharp ends, or edges 95. By providing sharp points 99 extending along the leading face of tip 88, a more aggressive cutting surface is provided on the tip for, e.g., cutting through the vessel wall.

In this embodiment, radii 96 are defined at this distal leading end of the tip between respective points 99. Preferably, this radius extends radially inwardly a distance R2 (FIG. 11) of between about 0.050 and 0.080 inch, and more preferably, about 0.070 inch, measured from an axial midpoint between adjacent points 99. These radii ranges are only examples, and those skilled in the art will appreciate other dimensions may be provided in an appropriate case. It is desirable to maintain a dimension R2 such that an aggressive leading face for vessel entry is provided, while at the same time not providing an exaggerated radius that may cause damage to the vessel.

If desired, selected portions of the lead extraction devices described herein, such as the tip portion, can be provided with imaging means for use with, e.g., x-ray or ultrasound. Such means are well known in the art, and may include, for example, the incorporation of a radiopaque and/or echogenic feature into a selected portion of the tip. Increased visibility of the tip may be beneficial, as it provides the operator with the ability to determine the location of the tip at a particular point in time. In addition, it provides the operator with the ability to track the position and orientation of the tip with reference to the lead body.

Those skilled in that art will appreciate that the foregoing detailed description should be regarded as illustrative rather than limiting, and that it should be understood that it is the following claims, including all equivalents, that are intended to define the spirit and scope of this invention.

What is claimed is:

1. A tip engageable with an elongated sheath for extracting an implanted structure from an obstruction in a body vessel of a patient, the elongated sheath having a distal end and a passageway extending at least substantially therethrough, the tip comprising:

a tip body having a proximal portion, a distal portion, a distal end having a substantially flat axial leading face extending circumferentially therearound, a chamfered inner circumferential edge extending inwardly and proximally from the axial leading face, and a passageway extending therethrough, said tip body proximal portion engageable with said sheath distal end, said respective passageways dimensioned and aligned such that the implanted structure is receivable therein, said tip body distal portion comprising a plurality of sides disposed around a circumference thereof, each of said sides comprising a pair of radially outwardly directed ends and an inwardly directed radiused portion between said ends, wherein each of said ends defines a unitary axial sharp edge configured to engage and separate an implanted structure from an obstruction in a body vessel of a patient, said unitary axial sharp edge extending parallel to a longitudinal axis of said tip body, and wherein each of said radiused portions comprises a continuous curvilinear concave surface that intersects a pair of adjacent axial sharp edges, and wherein said tip is configured to rotate about and relative to the implanted structure.

2. The tip of claim 1, wherein said tip body distal portion comprises between about 7 and 13 sides, each of said sides having substantially the same configuration and being sequentially disposed around said circumference.

3. The tip of claim 2, wherein said tip body distal portion comprises 10 sides.

4. The tip of claim 1, wherein said radiused portion extends radially inwardly a distance between about 0.006 and 0.012 inch from an axial midpoint between said respective ends.

5. The tip of claim 4, wherein said radially inward distance is between about 0.008 and 0.010 inch.

6. The tip of claim 1, wherein said chamfered inner circumferential edge comprises a radiused edge.

7. The tip of claim 1, wherein each said sharp edge intersects with said substantially flat leading face to define a point configured to facilitate disruption of said implanted structure from said obstruction upon a rotation of said tip.

8. The tip of claim 1, wherein said tip body has a smaller diameter proximal portion and a larger diameter distal portion, said smaller diameter proximal portion sized and configured for engagement with an inner surface of said sheath distal end, and wherein said tip body distal portion has a maximum outer diameter that is configured to be substantially similar to an outer diameter of said sheath distal end.

9. The tip of claim 8, wherein said tip body smaller diameter proximal portion includes an attachment member configured for engaging said inner surface of said sheath distal end.

10. The tip of claim 8, wherein the tip body distal portion has an axial length of between about 0.03 and 0.07 inch.

11. The tip of claim 8, wherein said larger diameter distal portion has a curved trailing surface at a junction with said small diameter proximal portion.

12. The tip of claim 1, wherein said tip ends are spaced along said circumference of said tip such that a constant length is provided between adjacent ends.

13. The tip of claim 12, wherein each inwardly directed radiused portion is of constant dimension along the circumference of the tip.

14. A device for extracting an elongated implanted structure from an obstruction within a vessel of a patient, comprising:
- an elongated sheath, said sheath having a constant outer diameter, and comprising a distal end and having a passageway extending therethrough, the sheath being sufficiently flexible to track over the implanted structure within the vessel; and
- a tip having a proximal portion, a distal portion, a substantially flat axial leading face extending circumferentially therearound, and a passageway extending therethrough, said tip proximal portion engaged with said sheath distal end such that said passageways are aligned to receive said implanted structure therein, said tip distal portion having an outer diameter substantially the same as the outer diameter of the elongated sheath, and having an axial length of between about 0.030 and 0.070 inch, said tip distal portion comprising between about 7 and 13 sides extending circumferentially therearound, each of said sides having a pair of radially outwardly directed ends comprising a unitary axial sharp edge extending parallel to a longitudinal axis of said tip body, and a continuous concaved surface extending between adjacent ends and intersecting the sharp edges thereof, each said end and pair of adjacent concave surfaces aligned to intersect with said substantially flat leading face to define a point configured to facilitate disruption of said implanted structure from said obstruction upon a rotation of said device, wherein each unitary axial sharp edge is configured to engage and separate an implanted structure from an obstruction in a body vessel of a patient,
- wherein at least the passageway of the tip is configured to be disposed over an elongated implanted structure disposed within a vessel of a patient, the tip being rotatable relative to the elongated implanted structure.

15. The device of claim 14, wherein said tip body distal portion comprises 10 sides having substantially identical configurations, and further comprising a circumferential chamfered inner edge extending inwardly and proximally from the flat axial leading face, the chamfered inner edge defining an outer periphery of the passageway of the tip.

16. A tip engageable with an elongated sheath for providing access to an interior of a vessel through an opening in a wall of the vessel for removing an elongated indwelling structure therefrom, the elongated sheath having a distal end and a passageway extending at least substantially therethrough, the tip comprising:
- a tip body having a proximal portion, a distal portion, and a passageway extending therethrough, said tip body proximal portion engageable with said sheath distal end, said respective passageways dimensioned and aligned such that the implanted structure is receivable therein, said tip body distal portion comprising a plurality of sides extending circumferentially therearound, said sides having respective radially outwardly directed ends each defining a unitary axially oriented sharp edge extending parallel to a longitudinal axis of said tip body, and a first radiused portion radially inwardly directed between adjacent ends, said first radiused portion defining a continuous concave surface intersecting said sharp edges of adjacent ends, said ends axially extending in a distal direction beyond a distal axial face of said tip body to respective distal points, and a second radiused portion proximally directed between adjacent points and defining a distal edge of the concave surface of each said side, wherein each unitary axially oriented sharp edge is configured to engage and separate an implanted structure from an obstruction in a body vessel of a patient,
- wherein the tip body is configured to be rotatably disposed over an elongated indwelling structure implanted within a vessel.

17. The tip of claim 16, wherein said tip body distal portion comprises between about 7 and 13 sides, each of said sides having substantially the same configuration.

18. The tip of claim 17, wherein said first radiused portion extends radially inwardly a distance between about 0.006 and 0.012 inch from an axial midpoint between the edges of said adjacent ends, and said second radiused portion extends proximally a distance between about 0.050 and 0.080 inch from an axial midpoint between said adjacent points.

19. The tip of claim 18, wherein said tip body portion comprises ten sides.

\* \* \* \* \*